US012779008B2

(12) United States Patent
Avva et al.

(10) Patent No.: US 12,779,008 B2
(45) Date of Patent: Nov. 3, 2026

(54) PROCESS FOR PURIFICATION OF MITRAGYNINE

(71) Applicant: LUCKY 4U EXIMS, Tirupati (IN)

(72) Inventors: Surya Pavan Kumar Avva, Tirupati (IN); V. S. R. Suresh Mamidipalli, Tirupati (IN)

(73) Assignee: LUCKY 4U EXIMS, Andhra Pradesh (IN)

( * ) Notice: Subject to any disclaimer, the term of this patent is extended or adjusted under 35 U.S.C. 154(b) by 532 days.

(21) Appl. No.: 18/311,707

(22) Filed: May 3, 2023

(65) Prior Publication Data

US 2024/0293496 A1 Sep. 5, 2024

(30) Foreign Application Priority Data

Feb. 17, 2023 (IN) ............................ 202341010930

(51) Int. Cl.
*A61K 36/74* (2006.01)
*A61K 31/4375* (2006.01)

(52) U.S. Cl.
CPC .......... *A61K 36/74* (2013.01); *A61K 31/4375* (2013.01); *A61K 2236/13* (2013.01); *A61K 2236/17* (2013.01); *A61K 2236/331* (2013.01); *A61K 2236/39* (2013.01); *A61K 2236/55* (2013.01)

(58) Field of Classification Search
CPC ................ A61K 36/74; A61K 2236/39; A61K 2236/55; A61K 2236/331; A61K 31/4375
See application file for complete search history.

(56) References Cited

U.S. PATENT DOCUMENTS

| | | | | |
|---|---|---|---|---|
| 3,932,417 | A | 1/1976 | Jones | |
| 2009/0247727 | A1* | 10/2009 | Bernabe | C07D 307/89 549/241 |
| 2017/0348222 | A1* | 12/2017 | Schafer Elejalde | A61K 8/31 |
| 2019/0330203 | A1* | 10/2019 | Tewari | A61K 36/24 |

FOREIGN PATENT DOCUMENTS

CN 101108872 A * 1/2008

OTHER PUBLICATIONS

Parthasarathy et al., Forensic Science International, 2013, 183-187.*
Sanchez-Soto et al., J Am Ceram Soc, 83, 7, 1649-1657, 2000.*
Goh et al Molecules, 26, 2021, 1-16.*
Mustafa et al. "Enhancing extraction yield and purity of Mitragynine from Mitragyna speciosa through sequential solvent extraction and characterisation using NMR technique." International Journal of Scientific & Technology Research. Mar. 2020. vol. 9, Issue 3. pp. 3846-3854.
Amrianto et al. "Mitragynine: a review of its extraction, identification, and purification methods." Current Research on Biosciences and Biotechnology. 2021. vol. 3, Issue 1. pp. 165-171.

* cited by examiner

*Primary Examiner* — Kyle A Purdy
(74) *Attorney, Agent, or Firm* — McCormick, Paulding & Huber PLLC

(57) ABSTRACT

The present invention discloses a process for the purification of Mitragynine, particularly discloses purification of Mitragynine from the crude extracts, for the pharmaceutical preparations. More particularly, the present invention discloses purification of Mitragynine using weak acid and weak base. The obtained purified Mitragynine is with fewer impurities.

23 Claims, 3 Drawing Sheets

Sample Information

Acquired by : Admin
Sample Name : 22-09-025-X-50-A[1]
Sample ID :
Tray# : 1
Vail# : 2
Injection Volume : 10 uL
Data Filename : 22-09-025-X-50-A[1].lcd
Method Filename : Mitragynine.lcm
Batch Filename : 271022.lcb
Report Filename : mitrya.lcr
Date Acquired : 27-Oct-22 1:29:42 PM
Data Processed : 27-Oct-22 9:57:52 PM Chromatogram
22-09-025-X-50-A[1] D:\LC-Solution\Data\2022-HPLC-1\OCT-10\271022\22-09-025-X-50-A[1].lcd

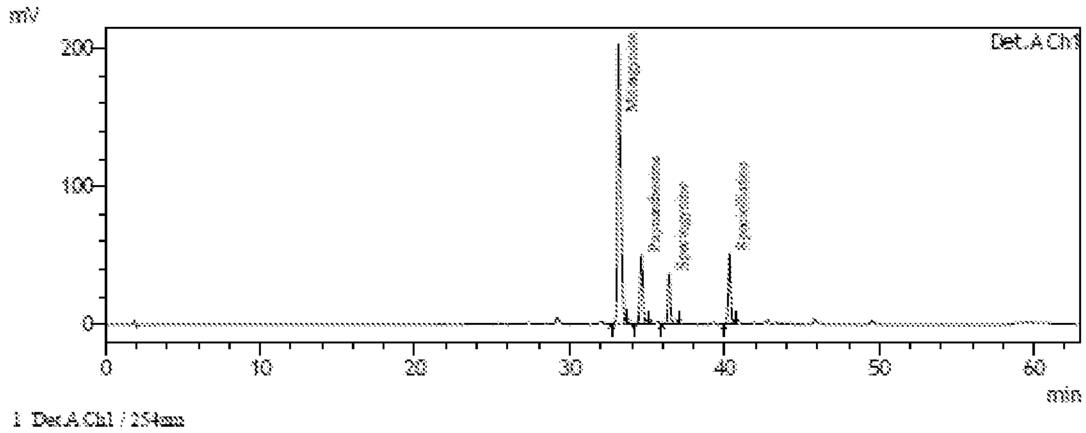

PeakTable D:\LC-Solution\Data\2022-HPLC-1\OCT-10\271022\22-09-025-X-50-A[1].lcd
Detector A Ch1 254nm

| Peak# | Name | Area | Height | Area % | Height % |
|---|---|---|---|---|---|
| 1 | Mitragynine | 3039203 | 202613 | 65.250 | 59.504 |
| 2 | Paynanthenine | 601900 | 50263 | 12.923 | 14.761 |
| 3 | Speciogynine | 421440 | 36309 | 9.048 | 10.663 |
| 4 | Speciolliatine | 595219 | 51320 | 12.779 | 15.072 |
| Total | | 4657762 | 340504 | 100.000 | 100.000 |

Figure 1

Sample Information

| | |
|---|---|
| Acquired by | : Admin |
| Sample Name | : 22-09-025-X-50-B[1] |
| Sample ID | : |
| Tray# | : 1 |
| Vail# | : 8 |
| Injection Volume | : 10 uL |
| Data Filename | : 22-09-025-X-50-B[1].lcd |
| Method Filename | : Mitragynine.lcm |
| Batch Filename | : 271022.lcb |
| Report Filename | : mitrya.lcr |
| Date Acquired | : 27-Oct-22 3:43:18 PM |
| Data Processed | : 27-Oct-22 5:59:22 PM |

Chromatogram
22-09-025-X-50-B[1] D:\LC-Solution\Data\2022-HPLC-1\OCT-10\271022\22-09-025-X-50-B[1].lcd

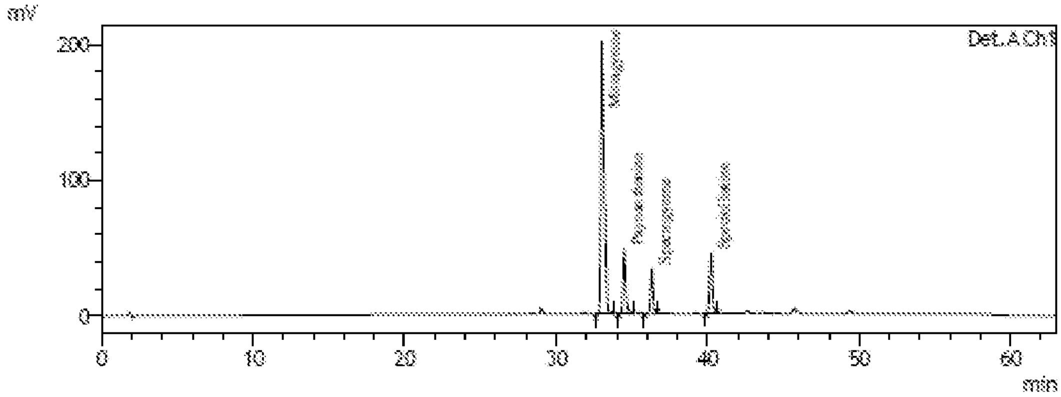

PeakTable D:\LC-Solution\Data\2022-HPLC-1\OCT-10\271022\22-09-025-X-50-B[1].lcd
Detector A Ch1 254nm

| Peak# | Name | Area | Height | Area % | Height % |
|---|---|---|---|---|---|
| 1 | Mitragynine | 2989519 | 201035 | 66.559 | 61.406 |
| 2 | Paynanthenine | 585392 | 47979 | 13.033 | 14.655 |
| 3 | Speciogynine | 392733 | 33513 | 8.744 | 10.236 |
| 4 | Speciolliatine | 523860 | 44860 | 11.663 | 13.703 |
| Total | | 4491503 | 327387 | 100.000 | 100.000 |

Figure 2

Sample Information

Acquired by : Admin
Sample Name : 22-09-025-X-50-C-1
Sample ID :
Tray# : 1
Vail# : 2
Injection Volume : 10 uL
Data Filename : 22-09-025-X-50-C-1.lcd
Method Filename : Mitragynine.lcm
Batch Filename : 281022.lcb
Report Filename : mitrya.lcr
Date Acquired : 28-Oct-22 12:50:06 PM
Data Processed : 28-Oct-22 5:30:09 PM Chromatogram
22-09-025-X-50-C-1 D:\LC-Solution\Data\2022-HPLC-1\OCT-10\281022\22-09-025-X-50-C-1.lcd

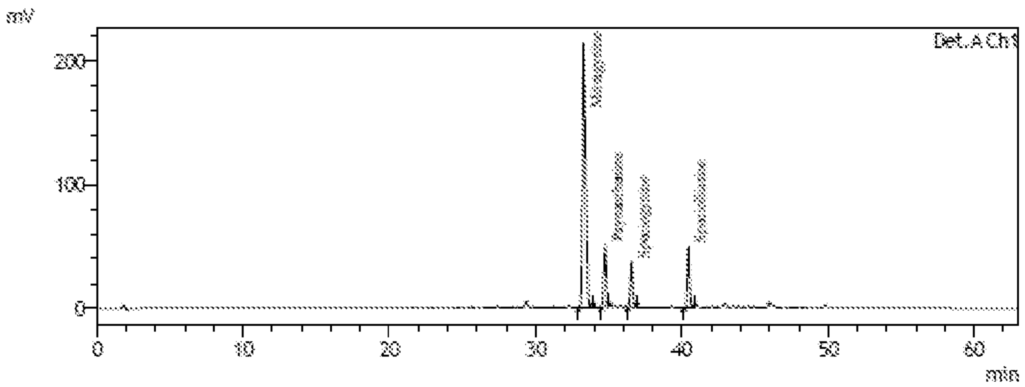

1 Det.A Ch1 / 254nm

PeakTable D:\LC-Solution\Data\2022-HPLC-1\OCT-10\281022\22-09-025-X-50-C-1.lcd
Detector A Ch1 254nm

| Peak# | Name | Area | Height | Area % | Height % |
|---|---|---|---|---|---|
| 1 | Mitragynine | 3138825 | 213850 | 67.309 | 61.159 |
| 2 | Paynanthenine | 561020 | 50083 | 12.031 | 14.323 |
| 3 | Speciogynine | 408612 | 36670 | 8.762 | 10.487 |
| 4 | Speciolliatine | 554848 | 49059 | 11.898 | 14.031 |
| Total | | 4663305 | 349662 | 100.000 | 100.000 |

Figure 3

PROCESS FOR PURIFICATION OF MITRAGYNINE

CROSS-REFERENCE TO RELATED APPLICATION

This application claims foreign priority benefits under 35 U.S.C. § 119 from Indian Patent Application No. 202341010930, filed Feb. 17, 2023, the content of which is hereby incorporated by reference in its entirety.

TECHNICAL FIELD

The present invention relates to a process for the purification of Mitragynine. Particularly the present invention relates to a process for purification of Mitragynine from the crude extracts, for the pharmaceutical preparations. More particularly, present invention relates to purification of Mitragynine using weak acid and weak base. The present invention also relates to the process of preparation of purified Mitragynine with fewer impurities.

BACKGROUND

Mitragynine is an indole-based alkaloid which is extracted from the leaves of *Mitragyna Speciosa* also known as Kratom. It has a chemical formula of C23H30N2O4 and an IUPAC name methyl (E)-2-[(2S,3S,12bS)-3-ethyl-8-methoxy-1,2,3,4,6,7,12,12b-octahydroindolo [2,3-a] quinolizin-2-yl]-3-methoxyprop-2-enoate. The chemical structure of Mitragynine is represented as:

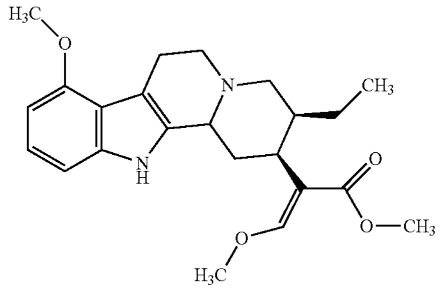 [SMILES: CC[C@@H]1CN2CCc3c([nH]c4cccc(OC)c34)C2C[C@@H]1/C(=C\OC)C(=O)OC]

Generally, Mitragynine is the most abundant alkaloid found in the leaves of *Mitragyna Speciosa* plants and has been used in herbal medicine and is also historically known for chewing and preparing tea. Kratom has opioid properties and exhibits stimulant-like effects. Mitragynine can be used for medicinal purposes particularly for pain management. It is also known for its use in recreational purposes and can be used in depression disorder, mood or anxiety disorders. Mitragynine is also suggested to reduce harmful opioid or other substance use and to manage withdrawal symptoms and cravings related to opioids and other drugs.

There have been many attempts to purify alkaloids using methods such as steam distillation, direct crystallization from solvent, chromatographic techniques such as column, paper or thin layer chromatography or gradient pH techniques. Even though attempts have been made in the prior arts to apply some of the techniques in purification of Mitragynine, these methods are time consuming, expensive or not suitable for industrial scale and inefficient. Further obtaining Mitragynine with fewer impurities and higher yield is not easy. Industrial purification of Mitragynine deals with larger volumes of the desired compounds at regulated temperatures, pressure, circulation etc. which is a challenge.

U.S. Pat. No. 3,932,417A discloses a process for the purification of indole alkaloids by using series of organic solvents followed by gel exclusion chromatography. The process of purification taught in this document is expensive when used at an industrial scale.

Radhiahtul Raehan Mustafa et. al., *Enhancing extraction yield and purity of Mitragynine from Mitragyna speciosa through sequential solvent extraction and characterisation using NMR technique. Int J Sci Technol Res* 9(3): 3846-54, March 2020, discloses separation of Mitragynine from the crude hexane-chloroform-MeOH extract using silica gel column chromatography. The solvent system used in column chromatography is hexane: EtOAc. Approximately 1.0 g of the crude extract was purified using column chromatography. The process of purification of Mitragynine taught in this disclosure employs column chromatography and can prove to be expensive.

None of the prior art teaches the efficient purification of Mitragynine extract with fewer impurities. Therefore, based on the existing prior arts there is not enough, or efficient processes of purification for crude Mitragynine or their derivatives. The existing limited prior arts on purification of Mitragynine are not suitable for industrial scale production of product. Further, using too many different solvents at each step makes the process tedious and not feasible at commercial level.

There is a need to design a purification process that would result in pure Mitragynine compound obtained at industrial scale with high economic significance. There is also a need to design a process that provides purified form of Mitragynine with fewer impurities that would help to improve efficacy of Mitragynine pharmaceutical preparations.

SUMMARY

The primary object of the present invention is to provide a process for the purification of Mitragynine suitable at industrial scale with high economic significance.

Another object of the invention is to provide a process for preparation of purified Mitragynine with fewer impurities.

Another object of the invention is to provide a process for purification of Mitragynine using weak acid and weak base.

Further object of the present invention is to provide purified Mitragynine for pharmaceutical applications.

Yet another object of the invention is to provide a process to give improved yield of Mitragynine free base (53% w/w) with purity of 47-53% by HPLC.

Recognizing the prior arts and need for improved process for purification of Mitragynine, in one aspect accordingly the present invention provides a process for the purification of Mitragynine comprising the steps of:

(a) mixing crude Mitragynine extract with a weak acid in a reactor followed by stirring;
(b) adding an alcohol to the mixture provided in step (a) followed by stirring;
(c) adding water to the mixture of step (b) while continuing the stirring;
(d) filtering the stirred solution as obtained in step (c) to obtain filtered solution and spent;
(e) optionally, adding weak acid and water to the spent obtained in step (d), followed by stirring and filtering, to obtain filtered solution;
(f) loading the filtered solution obtained in step (d) and/or step (e) into the reactor;

(g) adding a weak base to the filtered solution in the reactor of step (f) to maintain the pH 9 to 10;
(h) stirring the solution of step (g) until Mitragynine precipitate is formed;
(i) filtering the precipitated Mitragynine as obtained in step (h) followed by washing with water; and
(j) purifying washed precipitated Mitragynine as obtained in step (i) with alcohol, followed by drying to form purified Mitragynine free base.

The weak acid employed in the step (a) of the present process is selected from a group comprising of formic acid, benzoic acid, acetic acid, oxalic acid, or mixture thereof, preferably the weak acid employed in the step (a) is acetic acid.

In step (a) of the present process, the stirring is carried out for 15-30 minutes at 30-50 RPM.

The alcohol employed in the step (b) of the present process is selected from a group comprising of methanol, ethanol, propanol, butanol, isopropanol, iso butanol, tert-butanol, or mixture thereof, preferably the alcohol employed in the step (b) is methanol.

In step (b) of the present process, the stirring is carried out for 30 minutes at 30-50 RPM.

In step (c) of the present process, the stirring is carried out for 2 hours at 30-50 RPM.

In step (d) of the present process, filtering is carried out through cleaned nutsche filter on 5 microns cloth.

The weak base employed in step (g) of the present process, is selected from a group comprising of aluminium hydroxide, ferric hydroxide, liquor ammonia, pyridine, Methylamine, Trimethylamine, Aniline, or mixture thereof, preferably the weak base employed in step (g) is liquor ammonia.

In step (h) of the present process, the stirring is carried out for 30 minutes at 30-50 RPM.

In step (i) of the present process, precipitated Mitragynine is filtered through cleaned centrifuge with 200-250 RPM on 5 microns cloth.

In step (j) of the present process, alcohol is the dilute alcohol.

The alcohol employed in step (j) of the present process is selected from a group comprising of methanol, ethanol, propanol, butanol or mixture thereof, preferably the alcohol is methanol.

In step (j) of the present process, the alcohol is 10% methanol.

In step (j) of the present process, the product obtained after washing with alcohol is steam dried for 2 hours followed by drying in Vacuum Tray Dryer at 45-50° ° C. under 700 mm of Hg.

In some embodiment of the invention, there is provided a process for the purification of Mitragynine, said process comprises the steps of:
(a) mixing crude Mitragynine extract with acetic acid in a reactor followed by stirring at 30-50 RPM for 15-30 minutes at ambient temperature;
(b) adding methanol to the mixture provided in step (a) followed by stirring at 30-50 RPM for 30 minutes;
(c) adding water to the mixture of step (b) while continuing the stirring at 30-50 RPM for 2 hours;
(d) filtering the stirred solution as obtained in step (c) to obtain filtered solution and spent;
(e) optionally, adding acetic acid and water to the spent obtained in step (d), followed by stirring and filtering, to obtain filtered solution;
(f) loading the filtered solution obtained in step (d) and/or step (e) into the reactor;
(g) adding liquor ammonia to the filtered solution in the reactor of step (f) to maintain the pH 9-10;
(h) stirring the solution of step (g) at 30-50 RPM for 30 minutes until Mitragynine precipitate is formed;
(i) filtering the precipitated Mitragynine as obtained in step (h) followed by washing with water for removal of ammonia traces in it; and
(j) purifying washed precipitated Mitragynine as obtained in step (i) with 10% methanol, followed by drying to form purified Mitragynine free base.

The obtained Mitragynine free base in the present process is in amorphous form.

The instant process provides improved yield of Mitragynine free base (53% w/w) with purity of 47-53% by HPLC.

In some embodiment of the invention, purified Mitragynine free base obtained according to present invention is suitable for the pharmaceutical preparations.

BRIEF DESCRIPTION OF THE DRAWINGS

FIG. 1 depicts an HPLC graph showing purity of obtained Mitragynine free base.

FIG. 2 depicts an HPLC graph showing purity of obtained Mitragynine free base.

FIG. 3 depicts an HPLC graph showing purity of obtained Mitragynine free base.

DETAILED DESCRIPTION

The following detailed description refers to the accompanying drawing that show, by way of illustration, specific details and embodiments in which the invention may be practised. These embodiments are described in sufficient detail to enable those skilled in the art to practise the invention. Other embodiments may be utilized, and changes may be made without departing from the scope of the invention. The various embodiments are not necessarily mutually exclusive, as some embodiments can be combined with one or more other embodiments to form new embodiments.

Unless defined otherwise, all technical and scientific terms used herein have the same meaning as commonly understood by one of ordinary skill in the art to which the methods belong.

Further the embodiments described herein can be understood more readily by reference to the following detailed description, examples, and drawings. Methods described herein are merely illustrative of the principles of the present invention and are not limited to the specific embodiments presented in the detailed description, examples, and drawings. Numerous modifications and adaptations will be readily apparent to those of skill in the art without departing from the spirit and scope of the invention.

Where a range of values is provided, it is understood that each intervening value between the upper and lower limit of that range and any other stated or intervening value in that stated range, is encompassed within by the methods. The upper and lower limits of these smaller ranges may independently be included in the smaller ranges and are also encompassed within by the methods, subject to any specifically excluded limit in the stated range. Where the stated range includes one or both of the limits, ranges excluding either or both of those included limits are also included in the methods.

There are several methods known in the prior art for extracting Mitragynine. Some of the widely used methods of extraction of Mitragynine are Accelerated Solvent Extraction (ASE), Sequential Solvent Extraction, Soxhlet Extraction method etc. Further, in some prior arts the raw material is treated with some of the solvents for extraction followed by ion exchange chromatography or column chromatography for high purity of Mitragynine. The crude extract of Mitragynine obtained by the known extraction processes as described above, is used for purification process as disclosed in the present invention. The crude extracts can be purified to obtain high quality Mitragynine.

Accordingly, in one aspect the present invention discloses and describes a process for purification of Mitragynine using weak acid and weak base. The pure form of Mitragynine obtained in the present invention using the present process has fewer impurities and is economically significant.

The present process for purification of Mitragynine comprises first forming Mitragynine salt by reacting crude Mitragynine extract with weak acid followed by precipitation of Mitragynine free base on reaction with weak base.

The present process provides improved yield of Mitragynine (53% w/w) with purity of 47-53% by HPLC.

In one aspect of the invention, there is provided a process for the purification of Mitragynine comprising the steps of:

(a) mixing crude Mitragynine extract with a weak acid in a reactor followed by stirring;
(b) adding an alcohol to the mixture provided in step (a) followed by stirring;
(c) adding water to the mixture of step (b) while continuing the stirring;
(d) filtering the stirred solution as obtained in step (c) to obtain filtered solution and spent;
(e) optionally, adding weak acid and water to the spent obtained in step (d), followed by stirring and filtering, to obtain filtered solution;
(f) loading the filtered solution obtained in step (d) and/or step (e) into the reactor;
(g) adding a weak base to the filtered solution in the reactor of step (f) to maintain the pH 9 to 10;
(h) stirring the solution of step (g) until Mitragynine precipitate is formed;
(i) filtering the precipitated Mitragynine as obtained in step (h) followed by washing with water; and
(j) purifying washed precipitated Mitragynine as obtained in step (i) with alcohol, followed by drying to form purified Mitragynine free base.

The crude Mitragynine extract used in the present invention may be prepared by the methods known in the state of art. Traditionally known methods used for extraction of Mitragynine from plants includes maceration, percolation, reflux, Solvent Extraction, Soxhlet extraction. Amrianto et. al., *Mitragynine: a review of its extraction, identification, and purification methods, Current Research on Biosciences and Biotechnology* 3(1) 165-171, 2021, discloses various methods reported in the art for extracting Mitragynine, both conventional and renewable technology. Various extraction methods of Mitragynine reported in this literature are Solvent Extraction, Ultrasound assisted extraction (UAE), Accelerated solvent extraction (ASE) etc. The prepared crude extract of Mitragynine is purified by the process provided by the present invention.

Step (a):

In some embodiment of the invention, crude extract of Mitragynine is added slowly to the weak acid with continuous mixing followed by stirring.

The stirring the mixture of crude extract of Mitragynine and weak acid as mentioned in the step (a) may be carried out in 10 minutes to 2 hours, preferably 15 minutes to 1 hour, most preferably 15-30 minutes, 30-50 at RPM, preferably 38 RPM.

The step of adding crude extract of Mitragynine to the weak acid with continuous mixing followed by stirring may be carried out at ambient temperatures with jacket normal water cooling for reactor.

The weak acid employed in the step (a) may be selected from a group comprising of formic acid, benzoic acid, acetic acid, oxalic acid, or mixture thereof, preferably the weak acid employed in the step (a) is acetic acid.

By the addition of weak acid to the Mitragynine extract, Mitragynine salts are formed which are present in the solution obtained in the step (a). The Mitragynine salt as formed in step (a) depends upon the acid employed in the step (a). In one preferred embodiment of the invention, the Mitragynine salt formed in step (a) of the above-described process is formate salt, benzoate salt, acetate salt, oxalate salt, most preferably acetate salt.

Step (b):

In some embodiment of the invention, the stirring as mentioned in the step (b) may be carried out in 10 minutes to 1 hours, preferably 30 minutes, at 30-50 RPM, preferably 38 RPM.

The alcohol as mentioned in step (b) of present process is selected from a group comprising of methanol, ethanol, propanol, butanol, isopropanol, iso butanol, tert-butanol, or mixture thereof, preferably the alcohol is methanol.

Step (c):

In some embodiment of the invention, water is added to the alcoholic solution obtained in step (b) of the present process, followed by stirring.

The stirring as mentioned in the step (c) may be carried out for 1-4 hours, preferably 2-3 hours, most preferably 2 hours, at 30-50 RPM, preferably 38 RPM.

Due to addition of water to the alcoholic solution of Mitragynine salts, the soluble constituents such as salts of Mitragynine are passed into the aqueous phase. Whereas the organic phase carries the impurities in the crude extract of Mitragynine.

Step (d):

In some embodiment of the invention, filtering the stirred solution of step (c) as mentioned in step (d) of the above-described process may be done as known in the state of art. In one preferred embodiment the stirred solution of step (c) is filtered through cleaned nutsche filter on 5 microns cloth. The said filtration step results in separation of filtered solution and spent.

Step (e):

The spent obtained in step (d) of the present process can optionally be treated again with weak acid and water followed by stirring and filtering as defined above.

Step (f):

In one embodiment, the filtered solution obtained in step (d) is loaded into the reactor as mentioned in the step (f). In another embodiment, the filtered solution obtained in step (d) and step (e) are loaded into the reactor.

Steps (g) and (h):

In some embodiment of the invention, as mentioned in step (g) of the said process, the addition of weak base to the filtered solution in the reactor of step (f) maintains the pH 9 to 10.

In some embodiment of the invention, the addition of mixture of weak base to the filtered solution in the reactor of step (f) is followed by stirring until Mitragynine precipitate is formed.

The stirring as mentioned in the step (h) may be carried out in 10 minutes to 4 hours, preferably 10 minutes to 2 hours, preferably 30 minutes, at 30-50 RPM, preferably 38 RPM.

The weak base as mentioned in step (g) of present process is selected from a group comprising of aluminium hydroxide, ferric hydroxide, liquor ammonia, pyridine, Methylamine, Trimethylamine, Aniline, or mixture thereof, preferably the weak base is liquor ammonia.

When the aqueous layer comprising Mitragynine salt is mixed with ammonia, it makes the solution alkaline. Addition of ammonia converts Mitragynine salt to ammonium salt, which is soluble in water, freeing the Mitragynine free base. The free Mitragynine which is insoluble in water, is precipitated.

In one embodiment, following are the examples of various salts of ammonia (soluble in aqueous phase) and free Mitragynine (insoluble in water) are formed upon addition of ammonia free base to the filtered solution obtained in step (v):

Mitragynine acetate + ammonia free base = ammonium acetate + free Mitragynine precipitates. 1

Mitragynine formate + ammonia free base = ammonium formate + free Mitragynine precipitates. 2

Mitragynine benzoate + ammonia free base = ammonium benzoate + free Mitragynine precipitates. 3

Mitragynine oxalate + ammonia free base = ammonium oxalate + free Mitragynine precipitates. 4

Step (i):

In some embodiment of the invention, filtering the precipitated Mitragynine of step (h) as mentioned in step (i) of the above-described process may be done as known in the state of art. In one preferred embodiment the precipitated Mitragynine of step (h) is filtered through cleaned centrifuge with 200-250 RPM on 5 microns cloth.

In some embodiment of the invention, the precipitated Mitragynine after filtering as mentioned in the step (i) is washed with water for removal of ammonia traces in it. Ammonia being soluble in water, while the insoluble Mitragynine precipitate becomes relatively free of ammonia.

Step (j):

In some embodiment of the invention, the purification of the precipitated Mitragynine of step (i) as mentioned in the step (j) is carried out in presence of alcohol. In some embodiment, the precipitated Mitragynine of step (i) is loaded into reactor and alcohol is added.

In one preferred embodiment the alcohol employed in step (j) is the dilute alcohol.

The alcohol employed in the step (j) may be selected from a group comprising of methanol, ethanol, propanol, butanol or mixture thereof. In one preferred embodiment of the invention, the alcohol employed in step (j) of the above-described process is methanol.

In some embodiment of the invention, the purification of the precipitated Mitragynine of step (i) as mentioned in the step (j) is carried out in presence of 5-20% methanol, preferably 5-15% methanol, most preferably 10% methanol.

The product obtained after purification with alcohol is dried by the processes as known in the state of art. Traditionally known methods for drying are sun drying, air drying, steam drying, contact drying, infrared drying, freeze-drying, fluidized bed drying, electric drying etc.

In one preferred embodiment, the product obtained after purification with alcohol in step (j) of the present process is steam dried for 2-5 hours and then loaded into Vacuum Tray Dryer at 45-50° C. under 700 mm of Hg to obtain high purity Mitragynine free base. Preferably the product obtained after purification with alcohol in step (j) of the present process is steam dried for 2 hours and then loaded into Vacuum Tray Dryer to obtain purified Mitragynine free base.

The present process is performed at an ambient temperature.

In some embodiment of the invention there is provided a process for purification of Mitragynine, wherein said process comprises the steps of:

(a) mixing crude Mitragynine extract with acetic acid in a reactor followed by stirring at 30-50 RPM for 15-30 minutes at ambient temperature;
(b) adding methanol to the mixture provided in step (a) followed by stirring at 30-50 RPM for 30 minutes;
(c) adding water to the mixture of step (b) while continuing the stirring at 30-50 RPM for 2 hours;
(d) filtering the stirred solution as obtained in step (c) to obtain filtered solution and spent;
(e) optionally, adding acetic acid and water to the spent obtained in step (d), followed by stirring and filtering, to obtain filtered solution;
(f) loading the filtered solution obtained in step (d) and/or step (e) into the reactor;
(g) adding liquor ammonia to the filtered solution in the reactor of step (f) to maintain the pH 9-10;
(h) stirring the solution of step (g) at 30-50 RPM for 30 minutes until Mitragynine precipitate is formed;
(i) filtering the precipitated Mitragynine as obtained in step (h) followed by washing with water for removal of ammonia traces in it; and
(j) purifying washed precipitated Mitragynine as obtained in step (i) with 10% methanol, followed by drying to form purified Mitragynine free base.

In one preferred embodiment, the product obtained after purification with 10% methanol in step (j) of the present process is steam dried for 2 hours and then loaded into Vacuum Tray Dryer to obtain purified Mitragynine free base.

The obtained Mitragynine free base in the present process is in light yellowish to pale yellowish amorphous form.

The instant process provides improved yield of Mitragynine free base (53% w/w) with purity of 47-53% by HPLC.

In some embodiment of the invention, purified Mitragynine free base obtained according to present invention is suitable for the pharmaceutical preparations.

Certain specific aspect and embodiment of the present invention will be explained in detail with reference to the following examples, which are provided only for purposes of illustration and should not be construed as limiting the scope of the invention in any manner.

EXAMPLES

Example 1: Purification of Mitragynine

Crude Mitragynine Extract:

Crude Mitragynine extract can be obtained by traditionally known methods such as maceration, percolation, reflux, Solvent Extraction, Soxhlet extraction etc. For the present process, the crude extract of Mitragynine was obtained by the novel process for extraction of Mitragynine from

*Mitragyna speciosa* plant, which is developed by the present inventor and is disclosed and filed separately in another Indian patent application No. IN 202341010687 filed in the Indian Patent Office on Feb. 17, 2023.

Preparation of Mitragynine Acetate Salt in the Aqueous Solution:

Acetic acid (120 litres) was added to the reactor. Crude Mitragynine extract (60 Kgs) was slowly added to the reactor and mixed with acetic acid followed by stirring for 15-30 minutes at 38 RPM. The Mitragynine from crude Mitragynine extract reacts with acetic acid to form Mitragynine acetate salt present in the resultant solution.

To this resultant solution methanol (30 Litres) was added followed by stirring for 30 minutes at 38 RPM. While maintaining the stirring at 38 RPM, water (600 litres) was added to the said methanolic salt solution. The solution was stirred for 2 hours at 38 RPM. On addition of water, Mitragynine acetate salt present in the solution was dissolved in the water.

The resultant solution is filtered through cleaned nutsche filter on 5 microns cloth to separate filtered solution and spent. Mitragynine acetate salt present in the solution was passed into the filtered solution. Whereas spent carries the impurities in the crude extract of Mitragynine.

Acetic acid (30 litres) and water (30 litres) was again added to the spent followed by stirring and filtering through cleaned nutsche filter on 5 microns cloth to obtain filtered solution.

The filtered solution obtained above was combined and loaded into the cleaned reactor.

Preparation of Precipitated Mitragynine Free Base:

Ammonia (approximately 300 litres) was added to the filtered solution loaded into the cleaned reactor to make the solution alkaline at pH 9-10. The obtained solution was stirred for 30 minutes at 38 RPM, until the Mitragynine free base precipitate is formed.

Ammonia converts Mitragynine acetate to ammonium acetate, which is soluble in water, freeing the Mitragynine free base. The free Mitragynine which is insoluble in water, is precipitated.

The precipitate Mitragynine was filtered through cleaned centrifuge with 200-250 RPM on 5 microns cloth. The obtained precipitate Mitragynine after filtration was washed with water to remove traces of Ammonia.

Purification of Mitragynine Free Base:

The obtained Mitragynine free base from the above method was loaded into the clean reactor. 10% of Methanol (120 Litres) was added to the reactor. The resultant solid was steam dried for 2 hours and then it was loaded into Vacuum Tray Dryer 45-50° C. under 700 mm of Hg to obtain purified light yellowish to pale yellowish amorphous solid powder of Mitragynine free base.

All the steps are performed at room temperature.

Yield: 53% w/w

Purity: 50% by HPLC.

What is claimed is:

1. A process for the purification of mitragynine comprising the steps of:

(a) mixing crude mitragynine extract with a weak acid in a reactor followed by stirring;

(b) adding an alcohol to the mixture provided in step (a) followed by stirring;

(c) adding water to the mixture of step (b) while continuing the stirring;

(d) filtering the stirred solution as obtained in step (c) to obtain filtered solution and spent;

(e) optionally, adding weak acid and water to the spent obtained in step (d), followed by stirring and filtering, to obtain filtered solution;

(f) loading the filtered solution obtained in step (d) and/or step (e) into the reactor;

(g) adding a weak base to the filtered solution in the reactor of step (f) to maintain the pH 9 to 10;

(h) stirring the solution of step (g) until mitragynine precipitate is formed;

(i) filtering the precipitated mitragynine as obtained in step (h) followed by washing with water; and (j) purifying the washed precipitated mitragynine as obtained in step (i) with an alcohol, followed by drying to form purified mitragynine free base wherein in step (j) the product obtained after washing with alcohol is steam dried for 2 hours followed by drying in vacuum tray dryer at 45-50° C. under 700 mm of Hg.

2. The process as claimed in claim 1, wherein weak acid employed in the step (a) is selected from a group comprising of formic acid, benzoic acid, acetic acid, oxalic acid, or mixture thereof.

3. The process as claimed in claim 1, wherein weak acid employed in the step (a) is acetic acid.

4. The process as claimed in claim 1, wherein in step (a) the stirring is carried out for 15-30 minutes at 30-50 RPM.

5. The process as claimed in claim 1, wherein alcohol employed in the step (b) is selected from a group comprising of methanol, ethanol, propanol, butanol, isopropanol, iso butanol, tert-butanol, or mixture thereof.

6. The process as claimed in claim 1, wherein alcohol employed in the step (b) is methanol.

7. The process as claimed in claim 1, wherein in step (b) the stirring is carried out for 30 minutes at 30-50 RPM.

8. The process as claimed in claim 1, wherein in step (c) the stirring is carried out for 2 hours at 30-50 RPM.

9. The process as claimed in claim 1, wherein in step (d) filtering is carried out through cleaned nutsche filter on 5 microns cloth.

10. The process as claimed in claim 1, wherein weak base employed in step (g) is selected from a group comprising of aluminium hydroxide, ferric hydroxide, liquor ammonia, pyridine, methylamine, trimethylamine, aniline, or mixture thereof.

11. The process as claimed in claim 1, wherein weak base employed in step (g) is liquor ammonia.

12. The process as claimed in claim 1, wherein in step (h) the stirring is carried out for 30 minutes at 30-50 RPM.

13. The process as claimed in claim 1, wherein in step (i) precipitated mitragynine is filtered through cleaned centrifuge with 200-250 RPM on 5 microns cloth.

14. The process as claimed in claim 1, wherein the alcohol employed in step (j) is selected from a group comprising of methanol, ethanol, propanol, butanol or mixture thereof.

15. The process as claimed in claim 1, wherein in step the alcohol is methanol.

16. The process as claimed in claim 1, wherein in step the alcohol is aqueous 10% methanol solution v/v.

17. The process as claimed in claim 1, wherein the obtained mitragynine free base is in amorphous form.

18. The process as claimed in claim 1, wherein the purity of obtained mitragynine free base is 47-53% as determined by HPLC.

19. The process as claimed in claim 1, wherein said crude mitragynine extract is obtained from *Mitragyna speciosa*.

20. A process for the purification of mitragynine comprising the steps of:

(a) mixing crude mitragynine extract with acetic acid in a reactor followed by stirring at 30-50 RPM for 15-30 minutes at ambient temperature;

(b) adding methanol to the mixture provided in step (a) followed by stirring at 30-50 RPM for 30 minutes;

(c) adding water to the mixture of step (b) while continuing the stirring at 30-50 RPM for 2 hours;

(d) filtering the stirred solution as obtained in step (c) to obtain filtered solution and spent;

(e) optionally, adding acetic acid and water to the spent obtained in step (d), followed by stirring and filtering, to obtain filtered solution;

(f) loading the filtered solution obtained in step (d) and/or step (e) into the reactor;

(g) adding liquor ammonia to the filtered solution in the reactor of step (f) to maintain the pH 9-10;

(h) stirring the solution of step (g) at 30-50 RPM for 30 minutes until mitragynine precipitate is formed;

(i) filtering the precipitated mitragynine as obtained in step (h) followed by washing with water for removal of ammonia traces in it; and (j) purifying the washed precipitated mitragynine as obtained in step (i) with aqueous 10% methanol solution v/v, followed by drying to form purified mitragynine free base wherein in step (i) the product obtained after washing with alcohol is steam dried for 2 hours followed by drying in vacuum tray dryer at 45-50° C. under 700 mm of Hg.

21. The process as claimed in claim 20, wherein the obtained mitragynine free base is in amorphous form.

22. The process as claimed in claim 20, wherein the purity of obtained mitragynine free base is 47-53% by HPLC.

23. The process as claimed in claim 20, wherein said crude mitragynine extract is obtained from *Mitragyna speciosa.*

* * * * *